US006455704B1

(12) United States Patent
Hlatky

(10) Patent No.: US 6,455,704 B1
(45) Date of Patent: Sep. 24, 2002

(54) PROCESS FOR THE PREPARATION OF BASE-FREE CARBAZOLIDE ANIONS

(75) Inventor: Gregory G. Hlatky, Morrow, OH (US)

(73) Assignee: Equistar Chemicals L.P., Houston, TX (US)

( * ) Notice: Subject to any disclaimer, the term of this patent is extended or adjusted under 35 U.S.C. 154(b) by 0 days.

(21) Appl. No.: 09/947,581

(22) Filed: Sep. 6, 2001

(51) Int. Cl.$^7$ .............................. C07F 1/00; C07F 1/04; C07F 1/06
(52) U.S. Cl. ........................................ 548/440
(58) Field of Search ......................... 548/440

(56) References Cited

U.S. PATENT DOCUMENTS 5,539,124 A * 7/1996 Etherton and Nagy ..... 548/402

OTHER PUBLICATIONS

Bock et al. Carbazole deprotonation by sodium metal mirror in various ehters: structures with Na+–coordination nos. 3 and 4 to 7. 1997. Journal of Organometallic Chemistry (548), 115–120.*

Appler, J. Organometal. Chem., 350 (1988) 217.

Hacker et al., Chem. Ber., 120 (1987) 1533.

* cited by examiner

*Primary Examiner*—Joseph K. McKane
*Assistant Examiner*—Rebecca Anderson
(74) *Attorney, Agent, or Firm*—Brooks & Kushman P.C.

(57) ABSTRACT

Base-free carbazolides are prepared rapidly and in high yield and purity by reaction of a carbazole reactant with alkyl lithium in the presence of a dibasic ligand to form an intermediate complex, followed by reacting the intermediate complex with alkali metal alkoxide.

11 Claims, No Drawings

PROCESS FOR THE PREPARATION OF BASE-FREE CARBAZOLIDE ANIONS

BACKGROUND OF THE INVENTION

1. Field of the Invention

The present invention pertains to a process for the convenient, high-yield preparation of base-free carbazolide anions.

2. Background Art

Carbazolide anions have numerous uses in synthetic organic and organometallic chemistry. As but one example, transition metal complexes of carbazolides are known to have catalytic activity, i.e. as polymerization catalysts for α-olefin polymerization as disclosed in U.S. Pat. 5,539,124. In the syntheses of these compounds, the metal chloride is allowed to react with two equivalents of carbazolide anion. However, syntheses of many carbazolide complexes and carbazole derivatives require the use of substantially base-free carbazolide anions, i.e. potassium carbazolide. The preparation of base-free compounds has proven difficult.

For example, the deprotonation of carbazole by butyl-lithium in a toluene or pentane solvent is slow and incomplete, perhaps due to the possibility of hydrogen bonding in the partially deprotonated reaction mixture. Appler (J. Organometal. Chem., 350 (1988) 217) reported that deprotonation of carbazole by butyllithium in toluene required refluxing at 110° C. With the addition of coordinating solvents such as tetramethylethylene diamine (TMEDA) in tetrahydrofuran (THF) or toluene solvent, deprotonation is more rapid and more complete. However, the product is a base-coordinated complex such as [Li(THF)$_2$][C$_{12}$H$_8$N] (Hacker et al., Chem. Ber., 120 (1987) 1533) or [Li(TMEDA)][C$_{12}$H$_8$N]. In subsequent reaction with Group 4 metal compounds such as TiCl$_4$, Zr$_4$Cl$_4$, HfCl$_4$, the Lewis base remains coordinated in the final product to form (C$_{12}$H$_8$N)$_2$MCl$_2$(L)$_2$ compounds where L is THF or ½ TMEDA. These products are difficult to characterize and subsequent chemistry is complicated by the presence of the solventing group.

It would be desirable to provide a synthesis of carbazolide salts which are free of Lewis bases, producing the carbazolide salt in reasonable yields and with reasonable reaction times.

SUMMARY OF THE INVENTION

It has now been surprisingly discovered that carbazolide ions free of Lewis bases and complexing neutral ligands can be prepared rapidly and in high yield by reacting carbazole with a deprotonating agent in hydrocarbon solvent in the presence of at least an equimolar amount of an aprotic coordinating ligand to form an intermediate complex, followed by reaction in hydrocarbon solvent in the presence of one equivalent of alkali alkoxide to yield the base-free alkali carbazolide.

DETAILED DESCRIPTION OF THE PREFERRED EMBODIMENT(S)

Any carbazole is believed to be useful in the present process. Preferred carbazoles correspond to the formula

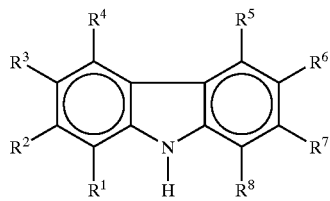

where $R^1$ through $R^8$ are hydrogen or substituents which do not interfere with obtaining the desired carbazolide anion product. Preferred $R^1$ through $R^8$ are hydrogen, alkyl, alkenyl, cycloalkyl, cycloalkenyl, alkoxy, polyoxyalkyl, aryl, heteroaryl, silyl, or two adjacent $R^1$ through $R^8$ may form a C$_{4-6}$ cycloalkyl or 6-membered aryl or heteroaryl ring or a C$_{4-6}$ cycloalkyl or 6 membered aryl or heteroaryl portion of a more extended ring system. Any of $R^1$ through $R^8$ and more preferably any of $R^2$ through $R^7$ and yet more preferably any of $R^3$ through $R^6$ may be an alkylene, alkenylene or silyl, etc. bridging linkage between a first carbazolide anion and a second carbazolide anion. Any one of C—$R^1$ to C—$R^8$ can also be replaced by a nitrogen, phosphorous, or arsenic atom.

Preferably, $R^1$ through $R^8$ are individually hydrogen, C$_{1-4}$ lower alkyl, or one or more pairs of adjacent $R^1$ through $R^8$ (including the pair of $R^4$ and $R^5$) may form an aryl or heteroaryl ring or an aryl or a heteroaryl portion of a larger aromatic ring system. Further examples of preferred carbazoles are found in U.S. 5,539,124, incorporated herein by reference. When $R^1$ through $R^8$ are alkyl, they are preferably C$_{1-4}$alkyl, more preferably methyl. It is preferred that $R^1$ and $R^8$ are hydrogen.

The hydrocarbon solvent in which the reaction takes place is a non-complexing hydrocarbon solvent which may also contain heteroatoms such as O, S, or N, as long as the heteroatoms do not facilitate strong complexing of the solvent with the carbazolide product. Most preferably, the solvent is an aromatic, aliphatic or cycloaliphatic hydrocarbon solvent. Preferred cycloaliphatic solvents include cyclopentane, cyclohexane, and cycloheptane. Preferred aliphatic solvents include pentane, hexane, heptane and their branched isomers. Preferred aromatic solvents include benzene, toluene, or o-, m-, or p- xylenes. Mixtures of solvents may be used. The preferred solvent is toluene. Coordinating solvents such as diethyl ether, tetrahydrofuran, and similar ether solvents can be used, but the intermediate lithium salt must be isolated from the reaction mixture for use in the second step of the reaction.

The coordinating ligand is a Lewis base-containing ligand, preferably an aprotic nitrogen-or oxygen-containing ligand. Preferred coordinating ligands include monobasic ligands such as tetrahydrofuran, 1,4-dioxane, and pyridine; chelating dibasic ligands such as N,N,N,N-tetramethylethylenediamine and ethylene glycol dimethyl ether; chelating tribasic ligands such as 1,3,5-trioxane and 1,3,5-trimethyl-1,3,5-triazine; and chelating tetrabasic ligands such as 12-crown-4. Dibasic and polybasic ligands containing both nitrogen and oxygen functionalities as well as ligands containing non-nitrogen and -oxygen complexing Lewis base atoms such as P, O, or S, may also serve as coordinating ligands.

The alkali alkoxide is one which is capable of destroying the intermediate lithium carbazolide/dibasic ligand complex. In general, the alkali alkoxide may be selected from sodium, potassium, and cesium alkoxides, but is preferably a potassium alkoxide. The alkoxide ion may have 1 to 10 or more carbon atoms, thus including methoxide, ethoxide, n-propoxide, isopropoxide, n-butoxide, i-butoxide, s-butoxide, t-butoxide, and other ions derived from linear, branched, or cyclic alkanols. The length of the carbon chain should be such that the resultant lithium alkoxide is soluble in aliphatic, cycloaliphatic, or aromatic solvents. Preferably, the alkali alkoxide is potassium t-butoxide.

The reaction may take place in one or more stages and will be described with reference to the preferred preparation using carbazole and TMEDA as the coordinating ligand. First, the carbazole is reacted in hydrocarbon solvent with alkyl lithium, preferably n-butyl lithium, in the presence of an equimolar amount of TMEDA, at a convenient temperature, i.e. from −20° to 50° C., preferably, 0° C. to 25° C. The reaction takes place preferably under moisture-free conditions, preferably under an inert gas blanket, i.e. of nitrogen, argon, etc. Solvents should be dried by conventional techniques. Following the reaction, the complex [Li (TMEDA)][$C_{12}H_8N$] may be collected as a white crystalline solid, substantially free of starting material. The intermediate may be separated and washed with additional solvent, or may be retained in the reaction solvent without isolation. If isolated, the intermediate is slurried in toluene or other solvent and reacted with one equivalent of potassium t-butoxide. This reaction may be carried out at temperatures from 0° C. to reflux, preferably room temperature to reflux. Potassium carbazolide is isolated as a white crystalline solid and optionally washed with additional solvent to remove all traces of lithium alkoxide. Lithium t-butoxide washes away in the solvent, having substantially pure potassium carbazolide. $^1$H NMR generally shows no trace of starting material.

Having generally described this invention, a further understanding can be obtained by reference to certain specific examples which are provided herein for purposes of illustration only and are not intended to be limiting unless otherwise specified.

EXAMPLES

Deprotonation of Carbazole

Example 1

Carbazole (3.34 g) was dissolved in tetrahydrofuran (50 mL) and butyllithium (8 mL of a 2.5 M solution in hexane) added. After 30 minutes, the solids were filtered off, washed with pentane, and dried. Yield: 4.79 g. This product was suspended in toluene (100 mL) and potassium t-butoxide (1.69 g) added. The mixture was refluxed for two hours and the pure-white solids filtered hot, washed with toluene and pentane and dried. Yield: 3.04 g. The $^1$H NMR spectrum of this product showed no residual N-H proton resonances.

Example 2

Carbazole (3.34 g) and N,N,N,N-tetramethylethylenediamine (2.32 g) were stirred in toluene (80 mL). Butyllithium (8 mL of a 2.5 M solution in hexane) was added. After 2 hours, the solution was evaporated to 20 mL and pentane added. The product was filtered off, washed with pentane and dried. Yield: 5.00 g. This was suspended in toluene (100 mL) and potassium t-butoxide (1.93 g) added. The mixture was refluxed for 2 hours and cooled. The pure-white product was filtered off, washed with toluene and pentane and dried. Yield: 3.35 g. The $^1$H NMR spectrum of this product showed no residual N-H proton resonances.

Comparative Example 3

Carbazole (1.67 g) was suspended in toluene (80 mL) and butyllithium (4 mL of a 2.5 M solution in hexane) added. The mixture was vigorously stirred at room temperature for 2 hours, forming a thick brownish gel. The solids were filtered off with difficulty, washed with pentane, and dried. The $^1$H NMR spectrum of this product showed residual N-H proton resonances at δ9.89.

Synthesis of Metal Complexes

Example 4

The product of Example 1 was slurried in toluene (50 mL) and added to a suspension of zirconium tetrachloride (1.73 g) in toluene (75 mL). The bright-yellow suspension was stirred overnight, then refluxed for two hours. The solids were filtered hot, washed with toluene and pentane and dried. Yield: 4.85 g.

Comparative Example 5

Carbazole (5.00 g) was suspended in toluene (60 mL) and butyllithium (12 mL of a 2.5 M solution in hexane) added. The mixture was vigorously stirred for two hours and additional toluene (60 mL) added, followed by zirconium tetrachloride (3.5 g). The green-brown slurry was stirred overnight, filtered, washed with toluene and pentane, and dried. Yield: 7.53 g.

Comparative Example 6

Carbazole (5.01 g) was suspended in toluene (120 mL) and butyllithium (12 mL of a 2.5 M solution in hexane) added. The mixture was vigorously stirred overnight. To the thick, light-brown slurry was added zirconium tetrachloride (3.5 g) with an additional aliquot of toluene (20 mL) to wash all the $ZrCl_4$ into the flask. The orange mixture was stirred for six hours, filtered, washed with toluene and pentane, and dried. Yield: 9.61 g.

Having now fully described the invention, it will be apparent to one of ordinary skill in the art that many changes and modifications can be made thereto without departing from the spirit or scope of the invention as set forth herein. The terms "a" and "an" mean one or more unless indicated otherwise.

What is claimed is:

1. A process for the preparation of alkali metal carbazolides, said process comprising a) reacting a carbazole reactant in a hydrocarbon solvent with alkyl lithium in the presence of one equivalent or more of an aprotic coordinating ligand, and optionally isolating an intermediate product comprising an aprotic ligand-coordinated lithium carbazolide;

b) reacting said intermediate product in hydrocarbon organic solvent with an alkali metal aloxide, said alkali metal selected from the group consisting of sodium potassium, rubidium, cesium, and mixtures thereof, thereby obtaining a corresponding alkali metal carbazolide product.

2. The process of claim 1, further comprising isolating said alkali metal carbazolide as a solid product.

3. The process of claim 2 further comprising washing said solid product with non-complexing organic solvent(s) to obtain an alkali metal carbazolide containing lesser amounts of impurties than the alkali metal carbazolide product obtained from said step of isolating.

4. The process of claim 1, wherein said carbazole has the formula

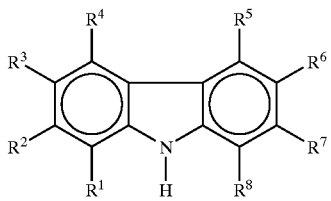

where $R^1$ through $R^8$ are individually hydrogen, alkyl groups, or other substituents which do not interfere with deprotonation of said carbazole with alkyl lithium, or where any two adjacent pairs of $R^1$ through $R^8$ together comprise a five or six membered ring system, optionally containing one or more heteroatoms, said ring system optionally being aromatic.

5. The process of claim 4, wherein each of substituents $R^1$ through $R^8$ of said carbazole is individually selected from hydrogen, $C_{1-4}$ lower alkyl, silyl, $C_{1-4}$ alkoxy, cyano, nitro, or where one or more adjacent pairs of $R^1$ through $R^8$ together comprise a $C_{5-6}$ saturated or unsaturated cycloaliphatic ring, or a $C_5$ or $C_6$ aryl or heteroaryl ring, said cycloaliphatic ring(s), aryl ring(s), and heteroaryl ring(s) optionally substituted with non-interfering substituents and optionally forming part of a larger alicyclic, aromatic, or alicyclicaromatic ring system.

6. The process of claim 1 wherein said alkyl lithium is n-butyl lithium.

7. The process of claim 1 wherein said alkali alkoxide is a potassium alkoxide.

8. The process of claim 1, wherein said alkali alkoxide is potassium t-butoxide.

9. The process of claim 1 wherein said hydrocarbon organic solvent is selected from the group consisting of toluene, xylene and mixture thereof.

10. The process of claim 1, wherein said carbazole reactant is carbazole, said alkyl lithium is n-butyl lithium, said alkali alkoxide is potassium t-butoxide, and wherein said solvent is a liquid aromatic hydrocarbon.

11. The process of claim 1 wherein said alkali metal carbazolide product is substantially free of basic complexing ligands.

* * * * *

UNITED STATES PATENT AND TRADEMARK OFFICE
CERTIFICATE OF CORRECTION

PATENT NO.     : 6,455,704 B1
DATED          : September 24, 2002
INVENTOR(S)    : Gregory G. Hlatky It is certified that error appears in the above-identified patent and that said Letters Patent is hereby corrected as shown below:

<u>Column 4,</u>
Line 54, after "hydrocarbon" delete "organic"
Line 54, delete "aloxide" and insert therefor -- alkoxide --.

Signed and Sealed this

Fourth Day of February, 2003

JAMES E. ROGAN
*Director of the United States Patent and Trademark Office*